United States Patent
Ondetti et al.

[11] 4,046,889
[45] Sept. 6, 1977

[54] AZETIDINE-2-CARBOXYLIC ACID DERIVATIVES

[75] Inventors: Miguel Angel Ondetti, Princeton; David W. Cushman, West Windsor, both of N.J.

[73] Assignee: E. R. Squibb & Sons, Inc., Princeton, N.J.

[21] Appl. No.: 657,792

[22] Filed: Feb. 13, 1976

[51] Int. Cl.² .................. C07D 205/08; A61K 31/395
[52] U.S. Cl. .................. 424/244; 260/326.2; 260/326.47; 260/293.73; 260/293.85; 260/239 A; 260/293.88; 260/293.86; 424/267; 424/274
[58] Field of Search .................. 260/239 A; 424/244

[56] References Cited
PUBLICATIONS

Thomas et al., Chem. Abs. 77, 33851w (1972).

*Primary Examiner*—Donald G. Daus
*Assistant Examiner*—Mark L. Berch
*Attorney, Agent, or Firm*—Lawrence S. Levinson; Merle J. Smith

[57] ABSTRACT

New proline derivatives and related compounds which have the general formula

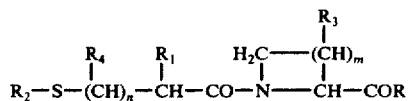

are useful as angiotensin converting enzyme inhibitors.

23 Claims, No Drawings

AZETIDINE-2-CARBOXYLIC ACID DERIVATIVES

SUMMARY OF THE INVENTION

This invention relates to new proline derivatives and related compounds which have the general formula

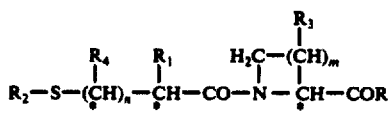

(I)

wherein

R is hydroxy, $NH_2$ or lower alkoxy;
$R_1$ and $R_4$ each is hydrogen, lower alkyl or phenyl-lower alkyl;
$R_2$ is hydrogen or $R_5$—CO;
$R_3$ is hydrogen, hydroxy or lower alkyl;
$R_5$ is lower alkyl, phenyl or phenyl-lower alkyl;
m is 1 to 3;
n is 0 to 2.

The asterisks indicate asymmetric carbon atoms. The carbon in the acyclic side chain is asymmetric when $R_1$ is other than hydrogen.

DETAILED DESCRIPTION OF THE INVENTION

The invention in its broad aspects includes proline and related derivatives having formula I above. Within this broad group, because of their properties, certain subgroups are preferred over others.

Broadly preferred are those compounds of formula I wherein R is hydroxy or lower alkoxy; $R_1$ is hydrogen or lower alkyl; $R_2$ is hydrogen or $R_5$—CO; $R_3$ and $R_4$ each is hydrogen; $R_5$ is lower alkyl, especially methyl, or phenyl; m is 2 and n is 0, 1 or 2, especially 1.

Especially preferred are those compounds which have the formula

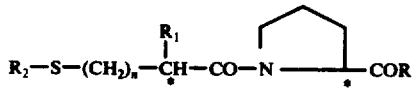

(II)

wherein

R is hydroxy or lower alkyl;
$R_1$ is hydrogen or lower alkyl;
$R_2$ is hydrogen or $R_5CO$;
$R_5$ is lower alkyl or phenyl, especially the first; and n is 0, 1 or 2.

Within the group of compounds represented by formula II, the following are still more preferred subgroups in the order (a to n) of increasing preference to the compounds which are especially preferred embodiments:

a. R is hydroxy
b. n is 1
c. $R_2$ is hydrogen or lower alkanoyl
d. $R_2$ is hydrogen
e. $R_2$ is acetyl
f. $R_1$ is hydrogen or lower alkyl
g. $R_1$ is hydrogen or methyl
h. R is hydroxy, $R_1$ is hydrogen or methyl
i. R is hydroxy, $R_1$ is hydrogen or methyl, $R_2$ is hydrogen or acetyl and n is 0, 1 or 2
j. R is hydroxy, $R_1$ and $R_2$ each is hydrogen and n is 0
k. R is hydroxy, $R_1$ is hydrogen, $R_2$ is acetyl and n is 1
l. R is hydroxy, $R_1$ is methyl, $R_2$ is acetyl and n is 1
m. R is hydroxy, $R_1$ and $R_2$ each is hydrogen and n is 1
n. R is hydroxy, $R_1$ is methyl, $R_2$ is hydrogen and n is 1

The stereoisomers in which the proline is in the L-form are especially preferred.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. The lower alkoxy groups are of the same kind having 1 to 7 carbons linked to oxygen, for example, methoxy, ethoxy, propoxy, isopropoxy, butoxy, isobutoxy, t-butoxy and the like. The $C_1$–$C_4$ members, especially $C_1$ and $C_2$ members, of both types are preferred. Phenylmethyl is the preferred phenyl-lower alkyl group.

The lower alkanoyl groups are those having acyl radicals of the lower ($C_2$–$C_7$) fatty acids, for example, acetyl, propionyl, butyryl, isobutyryl and the like. Similarly, those lower alkanoyl groups having up to four carbons, and especially acetyl, are preferred.

The products of formula I and the preferred subgroups can be produced by various methods of synthesis. According to a preferred method an acid or ester of the formula

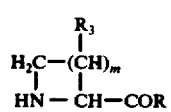

(III)

wherein R is hydroxy or lower alkoxy and $R_3$ is hydrogen, hydroxy or lower alkyl, e.g., proline, hydroxyproline, 4-methylproline, pipecolic acid, 4-hydroxypipecolic acid, azetidine-2-carboxylic acid or the like or lower alkyl esters thereof, is coupled with a haloalkanoic acid of the formula

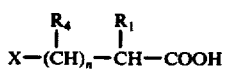

(IV)

wherein X is a halogen, preferably chlorine or bromine, by one of the known procedures in which the acid IV is activated, prior to reaction with the acid III, involving formation of a mixed anhydride, symmetrical anhydride, acid chloride, active ester, or use of Woodward reagent K, EEDQ (N-ethoxycarbonyl-2-ethoxy-1,2-dihydroquinoline) or the like.

The product of this reaction is a compound of the formula

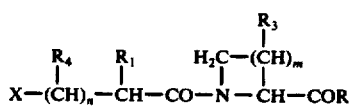

(V)

This product is subjected to a displacement reaction with the anion of a thioacid of the formula

(VI)

yielding a product of the formula

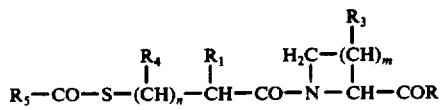
(VII)

which can then be converted to the product

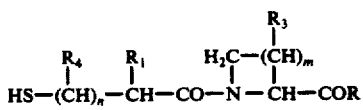
(VIII)

by ammonolysis. When R is an ester group (i.e., R is lower alkoxy), the ester group can be removed, e.g., when R is tert.butoxy or tert. amyloxy, treatment of the ester of formula VII or VIII with trifluoroacetic acid and anisole will give the corresponding free acid. When other alkoxy groups are present alkaline hydrolysis will yield the corresponding acid.

Variations of this procedure include the reaction of a thioacid of formula VI with an acrylic acid of the formula

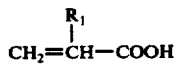
(IX)

to obtain the product

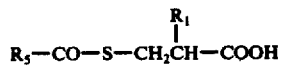
(X)

and this acid is coupled to the compound of formula III, or the acrylic acid of formula IX is first made to react with the compound of formula III to obtain a compound of the formula

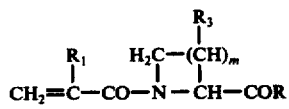
(XI)

and this intermediate is made to react with the thioacid VI. Ammonolysis is again used to obtain the product of formula I wherein $R_2$ is hydrogen.

More specifically and preferably, the acid or ester of formula III is made to react with a halo-alkanoyl halide of the formula

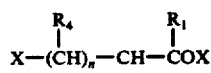
(XII)

wherein each X is independently a halogen, preferably chlorine or bromine, $R_1$ is hydrogen, lower alkyl or phenyl-lower alkyl and n is 0, 1 or 2. This reaction is effected in an alkaline medium, e.g., dilute alkali metal hydroxide solution, alkali metal bicarbonate or alkali metal carbonate solution at a reduced temperature, e.g., about 0° to 15° C. The reaction product is treated with the anion of the thio acid of the formula

$$R_5-CO-SH \quad (VI)$$

also in alkaline medium, preferably alkali metal carbonate solution, and then worked up in conventional manner. The product of this reaction, wherein $R_2$ of formula I is $R_5$—CO, is converted to the product wherein $R_2$ is hydrogen by ammonolysis, e.g., alcoholic ammonia or concentrated ammonium hydroxide solution. When an acid of formula III is used as starting material, the final product obtained as the free carboxylic acid can then be converted to its ester, for example by esterification with a diazoalkane, like diazomethane, 1-alkyl-3-p-tolyl-triazene, like 1-n-butyl-3-p-tolyltriazene or the like. Treatment of an ester, preferably the methyl ester, with an alcoholic ammonia solution, converts the free acid to the amide, i.e., R is $NH_2$.

According to another variation, an ester, preferably the t-butyl ester, of formula III, in an anhydrous medium such as dichloromethane, tetrahydrofuran, dioxane or the like, is treated with an acylthioalkanoic acid of the formula

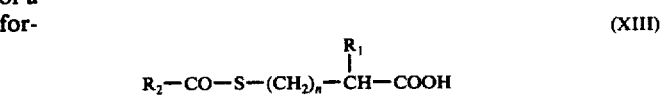
(XIII)

in the presence of dicyclohexylcarbodiimide, N, N'-carbonyl-bisimidazole, ethoxyacetylene, diphenylphosphoryl azide or similar coupling agents at a temperature in the range of about 0° to 10° C. The ester group (R) can then be removed, for example, by treatment with trifluoroacetic acid and anisole at about room temperature.

Alternatively, an ester of formula III (e.g., R is lower alkoxy, especially, t-butoxy) can be made to react with a thiolactone, e.g., β-propiothiolactone, α-methyl-β-propiothiolactone or the like in an anhydrous solvent like tetrahydrofuran, dioxane, methylene chloride or the like at about 0° C. to about room temperature. The ester group can be removed with anisole and trifluoroacetic acid as described above.

Products of formula I have one asymmetric carbon and two if $R_1$ is other than hydrogen. These carbon atoms are indicated by an asterisk in formula I. The compounds accordingly exist in stereoisomeric forms or in racemic mixtures thereof. All of these are within the scope of the invention. The above described synthesis can utilize the racemate or one of the enantiomers as starting material. When the racemic starting material is used in the synthetic procedure, the stereoisomers obtained in the product can be separated by conventional chromatographic or fractional crystallization methods. In general, the L-isomer with respect to the carbon of the amino acid constitute the preferred isomeric form.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product, as illustrated in the examples in the case of the dicyclohexylamine salt.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

Additional experimental details are found in the examples which are preferred embodiments and also serve as models for the preparation of other members of the group.

The compounds of this invention inhibit the conversion of the decapeptide angiotensin I to angiotensin II and therefore are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance present whichh has been implicated as the causative agent in various forms of hypertension in various mammalian species, e.g., rats and dogs. The compounds of this invention intervene in the renin→angiotensin I→• angiotensin II sequence by inhibiting angiotensin converting enzyme and reducing or eliminating the formation of the pressor substance angiotensin II. Thus by the administration of a composition containing one or a combination of compounds of formula I or physiologically acceptable salt thereof, angiotensin dependent hypertension in the species of mammal suffering therefrom is alleviated. A single dose, or preferably two to four divided daily doses, provided on a basis of about 0.1 to 100 mg. per kilogram per day, preferably about 1 to 50 mg. per kilogram per day is appropriate to reduce blood pressure as indicated in the animal model experiments described by S. L. Engel, T. R. Schaeffer, M. H. Waugh and B. Rubin, Proc. Soc. Exp. Biol. Med. 143, 483 (1973). The substance is preferably administered orally, but parenteral routes such as subcutaneously, intramuscularly, intravenously or intraperitonealy can also be employed.

The compounds of this invention can be utilized to achieve the reduction of blood pressure by formulating in compositions such as tablets, capsules or elixirs for oral administration or in sterile solutions or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples are illustrative of the invention and constitute especially preferred embodiments. All temperatures are in degrees celsius.

EXAMPLE 1

1-(2-Benzolthioacetyl)-L-Proline

L-Proline (5.75 g.) is dissolved in N sodium hydroxide (50 ml.) and the solution is chilled in an ice-water bath. Sodium hydroxide 2N (26 ml.) and chloroacetyl chloride (5.65 g.) are added and the mixture is stirred vigorously at room temperature for 3 hours. A suspension of thiobenzoic acid (7.5 g.) and potassium carbonate (4.8 g.) in water (50 ml.) is added. After 18 hours stirring at room temperature, the reaction mixture is acidified and extracted with ethyl acetate. The ethyl acetate layer is washed with water, dried over magnesium sulfate and concentrated to dryness in vacuo. The residue (14.6 g.) is dissolved in ethyl acetate (150 ml.) and dicyclohexylamine (11 ml.) is added. The crystals are filtered and recrystallized from ethyl acetate, yield 5.7 g. m.p. 151°-152°. To convert the salt to the acid, the crystals are dissolved in a mixture of 5% aqueous potassium bisulfate (100 ml.) and ethyl acetate (300 ml.). The organic phase is washed once with water, dried over magnesium sulfate and concentrated to dryness in vacuo, yield 3.45 g.

EXAMPLE 2

1-(2-Mercaptoacetyl)-L-Proline 1-(2-Benzoylthioacetyl)-L-proline (3.4 g.) is dissolved in a mixture of water (10.5 ml.) and concentrated ammonia (6.4 ml.). After 1 hour, the reaction mixture is diluted with water and filtered. The filtrate is extracted with ethyl acetate and then acidified with concentrated hydrochloric acid, saturated with sodium chloride and extracted twice with ethyl acetate. The ethyl acetate extracts are washed with saturated sodium chloride and concentrated to dryness, yield 1.5 g. The product, 1-(2-mercaptoacetyl)-L-proline is crystallized from ethyl acetate (m.p. 133°-135°).

EXAMPLE 3

1-(2-Benzoylthioacetyl)-L-Proline Methyl Ester 1-(2-Benzoylthioacetyl)-L-proline obtained in Example 1, is dissolved in methanol and an ethereal solution of diazomethane is added until there is a persistent yellow color. After 15 minutes, a few drops of acetic acid are added and the solvent is removed in vacuo to obtain 1-(2-benzoylthioacetyl)-L-proline methyl ester.

EXAMPLE 4

1-(2-Mercaptoacetyl)-L-Proline Amide

The product of Example 3 is dissolved in 10% methanolic ammonia and the solution is stored at room temperature in a pressure bottle. When thin layer chromatographic analysis indicates that the two ester functions have been ammonolyzed, the reaction mixture is concentrated to dryness to obtain 1-(2-mercaptoacetyl)-L-proline amide.

EXAMPLE 5

1-(2-Benzoylthioacetyl)-L-Hydroxyproline

By substituting L-hydroxyproline for the L-proline in the procedure of Example 1, 1-(2-benzoylthioacetyl)-L-hydroxyproline is obtained.

EXAMPLE 6

1-(2-Mercaptoacetyl)-L-Hydroxyproline

By treating the product of Example 5 with ammonia as in Example 2, 1-(-mercaptoacetyl)-L-hydroxyproline is obtained.

EXAMPLE 7

1-(2-Benzoylthioacetyl)-L-Azetidine-2-Carboxylic Acid

By substituting L-azetidine-2-carboxylic acid for the L-proline in the procedure of Example 1, 1-(2-benzoylthioacetyl)-L-azetidine-2-carboxylic acid is obtained.

EXAMPLE 8

1-(2-Mercaptoacetyl)-L-Azetidine-2-Carboxylic Acid

By treating the product of Example 7 with ammonia as in Example 2, 1-(2-mercaptoacetyl)-L-azetidine-2-carboxylic acid is obtained.

EXAMPLE 9

1-(2-Benzoylthioacetyl)-L-pipecolic Acid

By substituting L-pipecolic acid for the L-proline in the procedure of Example 1, 1-(2-benzoylthioacetyl)-L-pipecolic acid is obtained.

EXAMPLE 10

1-(2-Mercaptoacetyl)-L-Pipecolic Acid

By treating the product of Example 9 with ammonia as in Example 2, 1-(2-mercaptoacetyl)-L-pipecolic acid is obtained.

EXAMPLE 11

1-(2-Benzoylthiopropanoyl)-L-Proline

L-Proline (5.75 g.) is dissolved in aqueous N sodium hydroxide (50 ml.) and the solution is chilled in an ice bath with stirring. 2N sodium hydroxide (25 ml.) and 2-bromopropionyl chloride (8.57 g.) are added in that order and the mixture is removed from the ice bath and stirred at room temperature for 1 hour. A mixture of thiobenzoic acid (7.5 g.) and potassium carbonate (4.8 g.) in water (50 ml.) is added and the mixture is stirred overnight at room temperature. After acidification with concentrated hydrochloric acid, the aqueous solution is extracted with ethyl acetate and the organic phase is washed with water, dried and concentrated to dryness. The residue (14.7 g.) is chromatographed on a column of 440 g. of silica gel with a mixture of benzene-acetic acid (7:1). The fractions containing the desired material are pooled, concentrated to dryness, and the residue is precipitated twice with ether-hexane and converted to a dicyclohexylamine salt in ether-hexane, yield 9.4 g. m.p,, (142) 148°-156°. The dicyclohexylamine salt is converted back to the acid as in Example 1, yield 5.7 g.

EXAMPLE 12

1-(2-Mercaptopropanoyl)-L-Proline 1-(2-Benzoylthiopropanoyl)-L-proline (5.7 g.) is dissolved in a mixture of water (12 ml.) and concentrated ammonium hydroxide (9 ml.) with stirring. After 1 hour, the mixture is diluted with water (10 ml.) and filtered. The filtrate is extracted twice with ethyl acetate, concentrated to one-third of the original volume, acidified with concentrated hydrochloric acid and extracted wth ethyl acetate. The organic phase is washed with saturated sodium chloride, dried and concentrated to dryness in vacuo. The residue, 1-(2-mercaptopropanoyl)-L-proline, is crystallized from ethyl acetate-hexane, yield 3 g., m.p. (105) 116°-120°.

EXAMPLE 13

1-(3-Benzoylthiopropanoyl)-L-Proline

L-Proline (5.75 g.) is dissolved in normal sodium hydroxide (50 ml.) and the solution is chilled in an ice bath. 3-Bromopropionyl chloride (8.5 g.) and 2N sodium hydroxide (27 ml.) are added and the mixture is stirred for 10 minutes in the ice bath and three hours at room temperature. A suspension of thiobenzoic acid (7.5 g.) and potassium carbonate (4.5 g.) in water (50 ml.) is added and the mixture is stirred for 18 hours at room temperature. After acidification with concentrated hydrochloric acid, the aqueous phase is extracted twice with ethyl acetate. The organic layers are dried over magnesium sulfate and concentrated to dryness in vacuo to obtain 1-(3-benzoylthiopropanoyl)-L-proline, yield 7.1 g., m.p. 101°-102° (ethyl acetate-hexane).

EXAMPLE 14

L-Proline tert.-butyl ester

L-Proline (230 g.) is dissolved in a mixture of water (1 l.) and 5 N sodium hydroxide (400 ml.). The solution is chilled in an ice bath, and under vigorous stirring, 5 N sodium hydroxide (460 ml.) and benzyloxycarbonyl chloride (340 ml.) are added in five equal aliquots during a half hour period. After 1 hour stirring at room temperature, the mixture is extracted twice with ether and acidified with concentrated hydrochloric acid. The precipitate is filtered and dried. Yield 442 g. m.p. 78°-80°.

The benzyloxycarbonyl-L-proline thus obtained (180 g.) is dissolved in a mixture of dichloromethane (300 ml.), liquid isobutylene (800 ml.) and concentrated sulfuric acid (7.2 ml.). The solution is shaken in a pressure bottle for 72 hours. The pressure is released, the isobutylene is allowed to evaporate and the solution is washed with 5% sodium carbonate, water, dried over magnesium sulfate and concentrated to dryness in vacuo, to obtain benzyloxy-carbonyl-L-proline tert.butyl ester, yield 205 g.

Benzyloxycarbonyl-L-proline tert.butyl ester (205 g.) is dissolved in absolute ethanol (1.2 l) and hydrogenated at normal pressure with 10% Pd on carbon (10 g.) until only a trace of carbon dioxide is observed in the hydrogen exit gas (24 hours). The catalyst is filtered off and the filtrate is concentrated in vacuo at 30 mm. Hg. The residue is distilled in vacuo, to obtain L-proline tert.butyl ester, b.p.$_{1mm}$ 50°-51°.

EXAMPLE 15

1-(3-Acetylthiopropanoyl)-L-Proline tert-butyl Ester

L-Proline tert-butyl ester (5.13 g.) is dissolved in dichloromethane (40 ml.) and the solution is chilled in an ice-water bath. A solution of dicyclohexylcarbodiimide (6.18 g.) in dichloromethane (20 ml.) is added followed immediately by 3-acetylthiopropionic acid (4.45 g.). After 15 minutes stirring in the ice-water bath and 16 hours at room temperature, the precipitate is filtered off and the filtrate is concentrated to dryness in vacuo. The residue is dissolved in ethyl acetate and washed neutral. The organic layer is dried over magnesium sulfate and concentrated to dryness in vacuo to obtain 9.8 g. of 1-(3-acetylthiopropanoyl)-L-proline tert-butyl ester.

EXAMPLE 16

1-(3-Acetylthiopropanoyl)-L-Proline 1-(3-Acetylthiopropanoyl)-L-proline-t-butyl ester (4.7 g.) is dissolved in a mixture of anisole (34 ml.) and trifluoroacetic acid (68 ml.) and the mixture is kept at room temperature for 1 hour. The solvents are removed in vacuo and the residue is precipitated from ether-hexane several times. The residue (3.5 g.) is dissolved in acetonitrile (25 ml.) and dicyclohexylamine (2.8 ml.) is added. The crystalline salt is filtered and recrystallized from isopropanol. Yield 3.8 g.. m.p. 176°-177°. The salt is reconverted to 1-(3-acetylthiopropanoyl)-L-proline as in Example 1, yield 1.25 g., m.p. 89°-90° (ethyl acetate-hexane).

EXAMPLE 17

1-(3-Mercaptopropanoyl)-L-proline tert-butyl Ester

To a solution of L-proline tert-butyl ester (3.42 g.) in dry tetrahydrofuran (10 ml.) chilled in an ice bath, propiothiolactone (1.76 g.) is added. After 5 minutes storage in the ice bath and 3 hours at room temperature, the reaction mixture is diluted with ethyl acetate (200 ml.) and washed with 5% potassium bisulfate, and water. The organic layer is dried over magnesium sulfate and concentrated to dryness in vacuo. The residue 1-(3-mercaptopropanoyl)-L-proline tert-butyl ester is crystallized from ether-hexane, yield 3.7 g., m.p. 57°-58°.

EXAMPLE 18

1-(3-Mercaptopropanoyl)-L-Proline

Procedure A 1-(3-Benzoylthiopropanoyl)-L-proline (4.9 g.) is dissolved in a mixture of water (8 ml.) and concentrated ammonium hydroxide (5.6 ml.) and the solution is stored with stirring under argon for 1 hour. The reaction mixture is diluted with water, filtered, and the filtrate is extracted with ethyl acetate. The aqueous phase is acidified with concentrated hydrochloric acid, saturated with sodium chloride and extracted with ethyl acetate. The organic layers are washed with saturated sodium chloride, dried over magnesium sulfate, and concentrated to dryness in vacuo. The residue, 1-(3-mercaptopropanoyl)-L-proline, is crystallized from ethyl acetate hexane, yield 2.5 g., m.p. 68°-70°.

Procedure B 1-(3-Acetylthiopropanoyl)-L-proline (0.8 g.) is dissolved in 5.5 N methanolic ammonia (5 ml.) and the solution kept under argon at room temperature. After 2 hours the solvent is removed in vacuo, the residue is dissolved in water and applied to an ion exchange column on the H+ cycle [Dowex 50 (Analytical grade)] and eluted with water. The fractions that give thiol positive reaction are pooled and concentrated to dryness, yield 0.6 g. This product is crystallized from ethyl acetate-hexane as in Procedure A to obtain 1-(3-mercaptopropanoyl)-L-proline.

Procedure C 1-(3-Mercaptopropanoyl)-L-proline t-butyl ester (2.3 g.) is dissolved in a mixture of anisole (20 ml.) and trifluoroacetic acid (45 ml.). After 1 hour storage at room temperature under argon, the reaction mixture is concentrated to dryness in vacuo and the residue precipitated from ethyl acetatehexane several times. The residue (1.9 g.) is dissolved in ethyl acetate (30 ml.) and dicyclohexylamine (1.85 ml.) is added. The crystalline salt is filtered and recrystallized from isopropanol, yield 2 g. m.p. 187°-188°.

The salt is converted to the acid as in Example 1, yield 1.3 g. The product is crystallized from ethyl acetate hexane as in Procedure A.

Salts

Sodium 1-(3-Mercaptopropanoyl)-L-proline (500 mg.) is dissolved in a mixture of water (2.5 ml.) and N sodium hydroxide (2.5 ml.). The solution is freeze dried to obtain the sodium salt.

Magnesium 1-(3-Mercaptopropanoyl)-L-proline (500 mg.), magnesium oxide (49.5 mg.), and water (10 ml.) are stirred with slight heating until complete solution is obtained. Then the solvent is removed by freeze drying to obtain the magnesium salt.

Calcium 1-(3-Mercaptopropanoyl)-L-proline (500 mg.) is dissolved in a mixture of calcium hydroxide (91 mg.) and water (10 ml.), and the solution is freeze dried to obtain the calcium salt.

Potassium 1-(3-Mercaptopropanoyl)-L-proline (500 mg.) is dissolved in a mixture of potassium bicarbonate (246 mg.) and water (10 ml.) and freeze dried to obtain the potassium salt.

N-Methyl-D-Glucamine 1-(3-Mercaptopropanoyl)-L-proline (500 mg.) and N-methyl-D-glucamine (480 mg.) are dissolved in water (10ml.) and freeze dried to obtain the N-methyl-D-glucamine salt.

EXAMPLE 19

1-(3-Mercaptopropanoyl)-L-Hydroxyproline

By substituting L-hydroxyproline for the L-proline in the procedure of Example 11 and then treating the product by Procedure A of Example 18, 1-(3-benzoylthiopropanoyl)-L-hydroxyproline and 1-(3-mercaptopropanoyl)-L-hydroxyproline, respectively, are obtained.

EXAMPLE 20

1-(3-Mercaptopropanoyl)-L-Azetidine-2-Carboxylic Acid

By substituting L-azetidine-2-carboxylic acid tertbutyl ester (prepared by substituting L-azetidine-2-carboxylic acid for the proline in Example 14) for the L-proline tert-butyl ester in the procedure of Example 15, treating the product as in Example 16 and the 1-(3-acetylthiopropanoyl)-L-azetidine-2-carboxylic acid thus obtained by Procedure B of Example 18, 1-(3-acetylthiopropanoyl)-L-azetidine-2-carboxylic acid tert-butyl ester and 1-(3-mercaptopropanoyl)-L-azetidine-2-carboxylic acid, respectively, are obtained.

EXAMPLE 21

1-(3-Mercaptopropanoyl)-L-Pipecolic Acid

By substituting L-pipecolic acid tert-butyl ester (prepared by substituting L-pipecolic acid for the L-proline in Example 14) for the L-proline tert-butyl ester in the procedure of Example 15 and treating the product by Procedure C of Example 18, 1-(3-mercaptopropanoyl)-L-pipecolic acid tert-butyl ester and 1-(3-mercaptopropanoyl)-L-pipecolic acid, respectively, are obtained.

EXAMPLE 22

1-(3-Mercaptopropanoyl)-4-Methyl-L-Proline

By substituting 4-methyl-L-proline for L-proline in the procedure of Example 13 and then treating the product by Procedure A of Example 18, 1-(3-benzoylthiopropanoyl)-4-methyl-L-proline and 1-(3-mercaptopropanoyl)-4-methyl-L-proline, are obtained.

EXAMPLE 23

1-(3-Mercaptopropanoyl)-5-Hydroxy-L-Pipecolic Acid

By substituting 5-hydroxy-L-pipecolic acid for L-proline in procedure of Example 13 and then treating the product by the Procedure A of Example 18, 1-(3-benzoylthiopropanoyl)-5-hydroxy-L-pipecolic, and 1-(3-mercaptopropanoyl)-5-hydroxy-L-pipecolic acid are obtained.

EXAMPLE 24

1-(3-Mercaptopropanoyl)-D-Proline

By substituting D-proline for L-proline in the procedure of Example 13 and then treating the product by Procedure A of Example 18, 1-(3-benzoylthiopropanoyl)-D-proline and 1-(3-mercaptopropanoyl)-D-proline are obtained.

EXAMPLE 25

3-Acetylthio-2-Methylpropanoic Acid

A mixture of thioacetic acid (50 g.) and methacrylic acid (40.7 g.) is heated on the steam bath for 1 hour and then stored at room temperature for 18 hours. After confirming by nmr spectroscopy that complete reaction of the methacrylic acid has been achieved, the reaction mixture is distilled in vacuo and the desired 3-acetylthio-2-methylpropanoic acid is separated in the fraction with boiling point 128.5°–131° (2.6 mmHg.), yield 64 g.

EXAMPLE 26

3-Benzoylthio-2-Methylpropanoic Acid

By substituting thiobenzoic acid for the thioacetic acid in the procedure of Example 25, 3-benzoylthio-2-methylpropanoic acid is obtained.

EXAMPLE 27

3-Phenylcetylthio-2-Methylpropanoic Acid

By substituting thiophenylacetic acid for the thioacetic acid in the procedure of Example 25, 3-phenyl-acetylthio-2-methylpropanoic acid is obtained.

EXAMPLE 28

1-(3-Acetylthio-2-methylpropanoyl)-L-Proline tert-butyl Ester

L-Proline tert-butyl ester (5.1 g.) is dissolved in dichloromethane (40 ml.) and the solution stirred and chilled in an ice bath. Dicyclohexylcarbodiimide (6.2 g.) dissolved in dichloromethane (15 ml.) is added followed immediately by a solution of 3-acetylthio-2-methylpropanoic acid (4.9 g.) in dichloromethane (5ml.). After 15 minutes stirring in the ice bath and 16 hours at room temperature, the precipitate is filtered off and the filtrate is concentrated to dryness in vacuo. The residue is dissolved in ethyl acetate and washed neutral. The organic phase is dried over magnesium sulfate and concentrated to dryness in vacuo. The residue, 1-(3-acetylthio-2-methylpropanoyl)-L-proline tert-butyl ester, is purified by column chromatography (silica gel-chloroform), yield 7.9 g.

EXAMPLE 29

1-(3-Acetylthio-2-methylpropanoyl)-L-Proline

Procedure A

The 1-(3-acetylthio-2-methylpropanoyl)-L-proline tert-butyl ester of Example 28 (7.8 g.) is dissolved in a mixture of anisole (55 ml.) and trifluoroacetic acid (110 ml.). After 1 hour storage at room temperature the solvent is removed in vacuo and the residue is precipitated several times from ether-hexane. The residue (6.8 g.) is dissolved in acetonitrile (40 ml.) and dicyclohexylamine (4.5 ml.) is added. The crystalline salt is boiled with fresh acetonitrile (100 ml.), chilled to room temperature and filtered, yield 3.8 g., m.p. (165) 187°–188°. This material is recrystallized from isopropanol $[\alpha]_D - 67°$ (C 1.4, EtOH). The crystalline dicyclohexylamine salt is suspended in a mixture of 5% aqueous potassium bisulfate and ethyl acetate. The organic phase is washed with water and concentrated to dryness. The residue is crystallized from ethyl acetate-hexane to yield the 1-(3-acetyl-thio-2-D-methylpropanoyl-L-proline, m.p. 83°–85°$[\alpha]_D^{25} - 162(c, 1.7, EtOH)$.

Procedure B

3-Acetylthio-2-methylpropanoic acid (8.1 g.) and thionyl chloride (7 g.) are mixed and the suspension is stirred for 16 hours at room temperature. The reaction mixture is concentrated to dryness and distilled in vacuo (b.p. 80°). This 3-acetylthio-2-methylpropanoic acid chloride (5.4 g.) and 2N sodium hydroxide (15 ml.) are added to a solution of L-proline (3.45 g.) in normal sodium hydroxide (30 ml.) chilled in an ice water bath. After 3 hours stirring at room temperature, the mixture is extracted with ether, the aqueous phase is acidified and extracted with ethyl acetate. The organic phase is dried over magnesium sulfate and concentrated to dryness to obtain 1-(3-acetylthio-2-DL-methylpropanoyl-L-proline.

EXAMPLE 30

1-(3-Benzoylthio-2-methylpropanoyl)-L-proline tert-butyl Ester

By substituting 3-benzoylthio-2-methylpropanoic acid for the 3-acetylthio-2-methylpropanoic acid in the procedure of Example 28, 1-(3-benzoylthio-2-methylpropanoyl)-L-proline tert-butyl ester is obtained.

EXAMPLE 31

1-(3-Phenylacetylthio-2-methylpropanoyl)-L-Proline tert-butyl Ester

By substituting 3-phenylacetylthio-2-methylpropanoic acid for the 3-acetylthio-2-methylpropanoic acid in the procedure of Example 28, 1-(3-phenylcetylthio-2-methylpropanoyl)-L-proline tert-butyl ester is obtained.

EXAMPLE 32

1-(3-Benzoylthio-2-methylpropanoyl)-L-proline

By substituting 1-(3-benzoylthio-2-methylpropanoyl)-L-proline tert-butyl ester for the 1-(3-acetylthio)-2-methylpropanoyl)-1-proline tert-butyl ester in Procedure A of Example 29, 1-(3-benzoylthio-2-methylpropanoyl)-L-proline is obtained.

EXAMPLE 33

1-(3-Phenylacetylthio-2-methylpropanoyl)-L-proline

By substituting 1-(3-phenylacetylthio-2-methylpropanoyl)-L-proline tert-butyl ester for 1-(3-acetylthio-2-methylpropanoyl)-L-proline tert-butyl ester in Procedure A of Example 29, 1-(3-phenylacetylthio-2-methylpropanoyl)-L-proline is obtained.

EXAMPLE 34

1-(3-Mercapto-2-methylpropanoyl)-L-Proline 1-(3-Mercapto-2-methylpropanoyl)-L-proline is obtained by treating the product of each of Examples 29, 32 and 33 as follows:

The thioester (0.85 g.) is dissolved in 5.5 N methanolic ammonia and the solution is kept at room temperature for 2 hours. The solvent is removed in vacuo and the residue is dissolved in water, applied to an ion exchange column on the H+ cycle (Dowex 50, analytical grade) and eluted with water. The fractions that give positive thiol reaction are pooled and freeze dried. The residue is crystallized from ethyl acetate-hexane, yield 0.3 g. The 1-(3-mercapto-2-D-methylpropanoyl-L-proline has m.p. 103°-104°, $[\alpha]_D$ −131 (C,2,EtOH).

EXAMPLE 35

1-(3-Acetylthio-2-methylpropanoyl)-L-Proline Methyl Ester 1-(3-Acetylthio-2-methylpropanoyl)-L-proline is reacted with an ethereal solution of diazomethane according to the procedure described in Example 3 to obtain 1-(3-acetyl-thio-2-methylpropanoyl)-L-proline methyl ester.

EXAMPLE 36

1-(3-Mercapto-2-methylpropanoyl)-L-Proline amide

By substituting 1-(3-acetylthio-2-methylpropanoyl)-L-proline methyl ester in the procedure of Example 4, 1-(3-mercapto-2-methylpropanoyl)-L-proline amide is obtained.

EXAMPLE 37

3-Acetylthio-2-Benzylpropanoic Acid

By substituting 2-benzylacrylic acid for the methacrylic acid in the procedure of Example 25, 3-acetylthio-2-benzylpropanoic acid is obtained.

EXAMPLE 38

1-(3-Acetylthio-2-benzylpropanoyl)-L-Proline tert-butyl Ester

By substituting 3-acetylthio-2-benzylpropanoic acid for the 3-acetylthio-2-methylpropanoic acid in the procedure of Example 22, 1-(3-acetylthio-2-benzylpropanoyl)-L-proline tert-butyl ester is obtained.

EXAMPLE 39

1-(3-Acetylthio-2-benzylpropanoyl)-L-Proline

The product of Example 38 is substituted for the 1-(3-acetylthio-2-methylpropanoyl-L-proline tert-butyl ester in Procedure A of Example 29 to obtaine 1-(3-acetylthio-2-benzylpropanoyl)-L-proline.

EXAMPLE 40

1-(3-Mercapto-2-benzylpropanoyl)-L-Proline 1-(3-Acetylthio-2-benzylpropanoyl)-L-proline is treated with methanolic ammonia according to the procedure of Example 34 to obtain 1-(3-mercapto-2-benzylpropanoyl)-L-proline.

EXAMPLE 41

1-(3-Mercapto-2-methylpropanoyl)-L-Hydroxy Proline

By substituting L-hydroxy proline tert-butyl ester tert-butyl ether in the procedure of Example 28, treating the product accorrding to Procedure A of Example 29 and then continuing as in Example 34, 1-(3-acetylthio-2-methylpropanoyl)-L-hydroxyproline tert-butyl ester, tert-butyl ether, 1-(3-acetylthio-2-methylpropanoyl)-L-hydroxyproline and 1-(3-mercapto-2-methylpropanoyl)-L-hydroxyproline, respectively, are obtained.

EXAMPLE 42

1-(3-Mercapto-2-methylpropanoyl)-L-Azetidine-2-Carboxylic Acid

By substituting L-azetidine-2-carboxylic acid tert-butyl ester in the procedure of Example 28, treating the product according to Procedure A of Example 29 and then continuing as in Example 34, 1-(3-acetylthio-2-methylpropanoyl)-L-azetidine-2-carboxylic acid tert-butyl ester, 1(3-acetylthio-2-methyl-propanoyl)-L-azetidine-2-carboxylic acid and 1-(3-mercapto-2-methylpropanoyl)-L-azetidine-2-carboxylic acid are obtained.

EXAMPLE 43

1-(3-Mercapto-2-methylpropanoyl)-L-Pipecolic Acid

By substituting L-pipecolic acid in the procedure of Example 28, treating the product according to Procedure A of Example 29 and then cohtinuing as in Example 34, 1-(3-acetyl-thio-2-methylpropanoyl)-L-pipecolic acid tert-butyl ester, 1-(3-acetylthio-2-methylpropanoyl)-L-pipecolic acid and 1-(3-mercapto-2- methylpropanoyl)-L-pipecolic acid, respectively, are obtained.

EXAMPLE 44

1-(4-Benzoylthiobutanoyl)-L-Proline

To a solution of L-proline (2.88 g.) in normal sodium hydroxide (25 ml.) chilled in an ice bath, 2N sodium hydroxide (12.5 ml.) and 4-chlorobutyryl chloride (3.5 g.) are added. The reaction mixture is stirred at room temperature for 3.5 hours and a suspension of thiobenzoic acid (3.75 g.) and potassium carbonate (2.4 g.) in water (25 ml.) is added. After overnight stirring at room temperature, the reaction mixture is acidified with concentrated hydrochloric acid and extracted with ethyl acetate. The organic layer is dried over magnesium sulfate and concentrated to dryness in vacuo. The residue is chromatographed on a column of silica gel with benzene-acetic acid (7:1). The fractions containing the desired material are pooled and concentrated to dryness, yield 1.35 g. A small aliquot of this material is dissolved in ethyl acetate and dicyclohexylamine is added until pH 8-10 (on a wet pH paper). The dicyclohexylamine salt crystallizes out, immediately, m.p. 159°-161°.

EXAMPLE 45

1-(4-Mercaptobutanoyl)-L-Proline 1-(4-Benzylthiobutanoyl)-L-proline (1.08 g.) is dissolved in a mixture of water (4 ml.) and concentrated ammonia (2.7 ml.). After 1 hour stirring at room temperature, the mixture is diluted with water, filtered, extracted with ethyl acetate, and the aqueous phase was concentrated in vacuo. This ammonium salt of 1-(4-mercaptobutanoyl)-L-proline is purified by ion exchange chromatography on a column of diethyl-aminoethyl-Sephadex(cross linked dextran) with a gradient of ammonium bicarbonate, yield 0.7 g. The ammonium salt is dissolved in water (2ml.) and applied to a column of Dowex 50 sulfonic acid resin (analytical grade) in the hydrogen form, and the free acid is eluted with water. The fractions containing the desired material (sulfhydryl reagent and carboxyl reagent positive) are pooled and freeze dried to obtain 1-(4-mercaptobutanoyl)-L-proline.

EXAMPLE 46

4-Bromo-2-Methylbutanoic Acid

Ethyl-4-bromo-2-methylbutanoate [G. Jones and J. Wood, Tetrahedron, 21, 2961 (1965)] (1.04 g.) is dissolved in dichloromethane (50 ml.) and cooled to −10°. A 1 M solution of boron tribromide in dichloromethane (50 ml.) is added dropwise with stirring and the stirring is continued for 1 hour at −10° and 2 hours at 25°. The reaction is terminated by the careful addition of water. The layers are separated and the organic phase is washed with water, dried and concentrated to dryness to obtain 4-bromo-2-methylbutanoic acid.

EXAMPLE 47

1-(4-Benzoylthio-2-methylbutanoyl)-L-Proline a. 4-Bromo-2-methylbutanoic acid (8 g.) and thionyl chloride (7 g.) are mixed and the mixture is stirred for 16 hours at room temperature. The reaction mixture is concentrated to dryness and distilled in vacuo.

b. To a solution of L-proline (2.88 g.) in normal sodium hydroxide (25 ml.) chilled in an ice bath, 2N sodium hydroxide (12.5 ml.) and the 4-bromo-2-methylbutanoic acid chloride obtained in part (a) (3.9 g.) are added. The reaction mixture is stirred at room temperature for 3.5 hours and a suspension of thiobenzoic acid (3.75 g.) and potassium carbonate (2.4 g.) in water (25 ml.) is added. After overnight stirring at room temperature, the reaction mixture is acidified with concentrted hydrochloric acid and extracted with ethyl acetate. The organic layer is dried over magnesium sulfate and concentrated to dryness in vacuo. The residue is chromatographed on a column of silica gel with benzene-acetic acid (7:1). The fractions containing the desired product, 1-(4-benzoylthio-2-methylbutanoyl)-L-proline are pooled and concentrated to dryness in vacuo.

EXAMPLE 48

1-(4-Mercapto-2-methylbutanoyl)-L-Proline

By substituting 1-(4-benzoylthio-2-methylbutanoyl)-L-proline for the 1-(4-benzoylthiobutanoyl)-L-proline in the procedure of Example 45, 1-(4-mercapto-2-methylbutanoyl)-L-proline is obtained.

EXAMPLE 49

4-Bromo-2-benzylbutanoic acid

By substituting ethyl-4-bromo-2-benzylbutanoate [prepared by the procedure of G. Jones and J. Wood [Tetrahedron, 21, 2961 (1965) starting with diethylbenzylmalonate]] for the ethyl-4-bromo-2-methylbutanoate in the procedure of Example 46, 4-bromo-2-benzylbutanoic acid is obtained.

EXAMPLE 50

1-(4-Benzoylthio-2-benzylbutanoyl)-L-Proline

By substituting 4-bromo-2-benzylbutanoic acid for the 4-bromo-2-methylbutanoic acid in the procedure of Example 47, 1-(4-benzoylthio-2-benzylbutanoyl)-L-proline is obtained.

EXAMPLE 51

1-(4-Mercapto-2-benzylbutanoyl)-L-Proline

By substituting 1-(4-benzoylthio-2-benzylbutanoyl)-L-proline for the 1-(4-benzoylthiobutanoyl)-L-proline in the procedure of Example 45, 1-(4-mercapto-2-benzylbutanoyl)-L-proline is obtained.

EXAMPLE 52

1-(4-Mercaptobutanoyl)-L-Hydroxyproline

By substituting L-hydroxyproline for the L-proline in the procedure of Example 44 and subjecting the product to ammonolysis as in Example 45, 1-(4-benzoylthiobutanoyl)-L-hydroxyproline and 1-(4-mercaptobutanoyl)-L-hydroxyproline, respectively, are obtained.

EXAMPLE 53

1-(4-Mercaptobutanoyl)-L-Azetidine-2-Carboxylic Acid

By substituting L-azetidine-2-carboxylic acid for the L-proline in the procedure of Example 44 and subjecting the product to ammonolysis as in Example 45, 1-(4-benzoylthiobutanoyl)-L-azetidine-2-carboxylic acid and 1-(4-mercaptobutanoyl)-L-azetidine-2-carboxylic acid, respectively, are obtained.

EXAMPLE 54

1-(4-Mercaptobutanoyl)-L-Pipecolic Acid

By substituting L-pipecolic acid for the L-proline in the procedure of Example 44 and subjecting the product to ammonolysis as in Example 45, 1-(4-benzoylthiobutanoyl)-L-pipecolic acid and 1-(4-mercaptobutanoyl)-L-pipecolic acid, respectively, are obtained.

EXAMPLE 55

1-(3-Acetylthiobutanoyl)-L-Proline tert-butyl Ester

Dicyclohexylcarbodiimide (6.2 g.) and 3-acetylthiobutyric acid (4.86 g.) are added to a solution of L-proline tert-butyl ester (5.1 g.) in dichloromethane (60 ml.) stirred in an ice bath. After 15 minutes the ice bath is removed and the mixture is stirred at room temperature for 16 hours. The precipitate is filtered, the filtrate is concentrated to dryness and the residue is chromatographed on a column of silica gel with chloroform to obtain 1-(3-acetylthiobutanoyl)-L-proline tert-butyl ester, yield 5.2 g.

EXAMPLE 56

1-(3-Acetylthiobutanoyl)-L-Proline

The 1-(3-acetylthiobutanoyl)-L-proline tert-butyl ester of Example 55 (5.2 g.) is dissolved in a mixture of trifluoroacetic acid (60 ml.) and anisole (30 ml.) and the solution is kept at room temperature for 1 hour. The solvents are removed in vacuo and the residual 1-(3-acetylthiobutanoyl)-L-proline is reprecipitated from ether-hexane several times, yield 4 g.. The dicyclohexylamine salt is made by the procedure of Example 44, m.p. 175°–176°.

EXAMPLE 57

1-(3-Mercaptobutanoyl)-L-Proline

The 1-(3-acetylthiobutanoyl)-L-proline tert-butyl ester of Example 55 (0.86 g.) is dissolved in 5.5 N methanolic ammonia (20 ml.) and the reaction mixture is stored at room temperature for 2 hours. The solvent is removed in vacuo and the residue chromatographed on an ion exchange column (Dowex 50) with water. The fractions containing the desired 1-(3-mercaptobutanoyl)-L-proline are pooled and lyophilized, yield 0.6 g. The dicyclohexylamine salt is produced by the procedure of Example 44, m.p. 183°–184°.

The racemic forms of the final products in each of the foregoing examples are produced by utilizing the DL-form of the starting amino acid instead of the L-form.

Similarly, the D-form of the final products in each of the foregoing examples is produced by utilizing the D-form of the starting amino acid instead of the L-form.

EXAMPLE 58

1000 tablets each containing 100 mg. of 1-(2-mercapto-propanoyl)-L-proline are produced from the following ingredients:

| 1-(2-Mercaptopropanoyl)-L-proline | 100 | g. |
|---|---|---|
| Corn starch | 50 | g. |
| Gelatin | 7.5 | g. |
| Avicel (microcrystalline cellulose) | 25 | g. |
| Magnesium stearate | 2.5 | g. |

The 1-(2-mercaptopropanoyl)-L-proline and corn starch are admixed with an aqueous solution of the gelatin. The mixture is dried and ground to fine powder. The Avicel and then the magnesium stearate are admixed with the granulation. This is then compressed in a tablet press to form 1000 tablets each containing 100 mg. of active ingredient.

EXAMPLE 59

1000 tablets each containing 200 mg. of 1-(2-mercaptoacetyl)-L-proline are produced from the following ingredients:

| 1-(2-Mercaptoacetyl)-L-proline | 200 | g. |
|---|---|---|
| Lactose | 100 | g. |
| Avicel | 150 | g. |
| Corn Starch | 50 | g. |
| Magnesium stearate | 5 | g. |

The 1-(2-mercaptoacetyl)-L-proline, lactose and Avicel are admixed, then blended with the corn starch. Magnesium stearate is added. The dry mixture is compressed in a tablet press to form 1000 505 mg. tablets each containing 200 mg. of active ingredient. The tablets are coated with a solution of Methocel E 15 (methyl cellulose) including as a color a lake containing yellow No. 6.

EXAMPLE 60

Two piece No. 1 gelatin capsules each containing 250 mg. of 1-(2-mercaptopropanoyl)-L-proline are filled with a mixture of the following ingredients:

| 1-(2-Mercaptopropanoyl)-L-proline | 250 | mg. |
|---|---|---|
| Magnesium stearate | 7 | mg. |
| USP lactose | 193 | mg. |

EXAMPLE 61

An injectable solution is produced as follows:

| 1-(2-Mercaptopropanoyl)-L-proline | 500 | g. |
|---|---|---|
| Methyl paraben | 5 | g. |
| Propyl paraben | 1 | g. |
| Sodium chloride | 25 | g. |
| Water for injection qs. | 5 | l. |

The active substance, preservatives and sodium chloride are dissolved in 3 liters of water for injection and then the volume is brought up to 5 liters. The solution is filtered through a sterile filter and aseptically filled into presterilized vials which are then closed with pre-sterilized rubber closures. Each vial contains 5 ml. of solution in a concentration of 100 mg. of active ingredient per ml. of solution for injection.

What is claimed is:

1. A compound of the formula

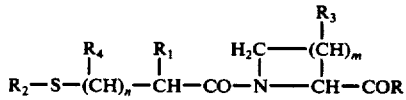

wherein

R is hydroxy, amino or lower alkoxy;

$R_1$ and $R_4$ each is hydrogen, lower alkyl or phenyl-lower alkyl;

$R_2$ is hydrogen or $R_5$—CO;

$R_3$ is hydrogen, hydroxy or lower alkyl;

$R_5$ is lower alkyl, phenyl or phenyl-lower alkyl;
$m$ is 1;
$n$ is 0, 1 or 2.
and basic salts thereof.

2. A compound as in claim 1 wherein R is hydroxy or lower alkoxy; $R_1$ is hydrogen or lower alkyl; $R_2$ is hydrogen or $R_5$—CO; $R_3$ and $R_4$ each is hydrogen; $R_5$ is lower alkyl or phenyl; $m$ is 1 and $n$ is 0, 1 or 2.

3. A compound as in claim 1 wherein $R_3$ and $R_4$ each is hydrogen.

4. A compound as in claim 1 wherein $m$ is 1 and $R_3$ is hydrogen.

5. The L-form of a compound of claim 1.

6. A compound as in claim 1 wherein R is hydroxy.

7. A compound as in claim 1 wherein $n$ is 1.

8. A compound as in claim 1 wherein $R_2$ is hydrogen or lower alkanoyl.

9. A compound as in claim 1 wherein $R_2$ is hydrogen.

10. A compound as in claim 1 wherein $R_2$ is acetyl.

11. A compound as in claim 1 wherein $R_1$ is hydrogen or lower alkyl.

12. A compound as in claim 1 wherein $R_1$ is hydrogen or methyl.

13. A compound as in claim 1 wherein R is hydroxy and $R_1$ is hydrogen or methyl.

14. A composition comprising a compound of claim 1 in an amount sufficient to reduce blood pressure by inhibiting the conversion of angiotension I to angiotension II and a pharmaceutically acceptable vehicle therefor.

15. A method for reducing blood pressure by inhibiting the conversion of angiotensin I to angiotensin II which comprises administering a composition comprising a compound of claim 1 in an amount sufficient to reduce blood pressure by inhibiting the conversion of angiotension I to angiotension II and a pharmaceutically acceptable vehicle therefor.

16. A compound as in claim 1 wherein $n$ is 0.

17. A compound as in claim 16 wherein R is hydroxy, $R_1$ and $R_3$ each is hydrogen and $R_2$ is benzoyl.

18. A compound as in claim 16 wherein R is hydroxy and $R_1$, $R_2$ and $R_3$ each is hydrogen.

19. A compound as in claim 7 wherein R is hydroxy and $R_1$, $R_2$, $R_4$ and $R_3$ each is hydrogen.

20. A compound as in claim 7 wherein R is hydroxy, $R_1$ is methyl and $R_2$, $R_4$ and $R_3$ each is hydrogen.

21. The compound of claim 18 wherein the azetidine is in the L-form.

22. The compound of claim 19 wherein the azetidine is in the L-form.

23. The compound of claim 20 wherein the azetidine is in the L-form.

* * * * *